United States Patent
Kang et al.

(10) Patent No.: US 12,059,257 B2
(45) Date of Patent: Aug. 13, 2024

(54) APPARATUS AND METHOD FOR GENERATING DRIVER SKILLED DRIVING MODEL USING ERROR MONITORING

(71) Applicants: HYUNDAI MOTOR COMPANY, Seoul (KR); KIA MOTORS CORPORATION, Seoul (KR); SOOKMYUNG WOMEN'S UNIVERSITY INDUSTRY-ACADEMIC COOPERATION FOUNDATION, Seoul (KR)

(72) Inventors: Jeong Su Kang, Seongnam-si (KR); Suh Yeon Dong, Seoul (KR)

(73) Assignees: HYUNDAI MOTOR COMPANY, Seoul (KR); KIA MOTORS CORPORATION, Seoul (KR); SOOKMYUNG WOMEN'S UNI INDUSTRY-ACADEMIC CO-OP FDN, Seoul (KR)

( * ) Notice: Subject to any disclaimer, the term of this patent is extended or adjusted under 35 U.S.C. 154(b) by 298 days.

(21) Appl. No.: 17/038,573

(22) Filed: Sep. 30, 2020

(65) Prior Publication Data
US 2021/0114599 A1    Apr. 22, 2021

(30) Foreign Application Priority Data
Oct. 22, 2019    (KR) .................. 10-2019-0131118

(51) Int. Cl.
G06G 7/70    (2006.01)
A61B 5/00    (2006.01)
(Continued)

(52) U.S. Cl.
CPC ................ *A61B 5/18* (2013.01); *A61B 5/165* (2013.01); *A61B 5/369* (2021.01); *A61B 5/7221* (2013.01);
(Continued)

(58) Field of Classification Search
CPC ................ B60W 40/08; B60W 30/00; B60W 2540/221; B60W 2420/42;
(Continued)

(56) References Cited

U.S. PATENT DOCUMENTS 8,805,489 B1 *  8/2014  Ofek ........................ A61B 5/38
                                                    600/544
10,521,677 B2 * 12/2019  Micks ..................... G06F 30/15
(Continued)

FOREIGN PATENT DOCUMENTS

| JP | 2011248535 A | 12/2011 |
| JP | 2017061192 A | 3/2017 |

(Continued)

OTHER PUBLICATIONS

KR-100696275-B1, Radio telemetric system and method using brain potentials for remote control of toy (Year: 2007).*

*Primary Examiner* — Naomi J Small
(74) *Attorney, Agent, or Firm* — MCDONNELL BOEHNEN HULBERT & BERGHOFF LLP

(57) ABSTRACT

Disclosed herein is an apparatus and method for generating a driving model. The driving model generation method includes sensing to collect a brain wave signal for a driver in a mobility for a predetermined time, determining the driver's state by analyzing the brain wave signal collected for the predetermined time, detecting at least one of operational information and driving information of the mobility on the basis of the determined state of the driver, and storing the detected information. Herein, the brain wave signal (Continued)

includes an event-related potential (ERP), and the determining includes determining, by analyzing the ERP, whether or not the driver is in an unstable state.

16 Claims, 11 Drawing Sheets

(51) Int. Cl.
  *A61B 5/16* (2006.01)
  *A61B 5/18* (2006.01)
  *A61B 5/369* (2021.01)
  *B60W 30/00* (2006.01)
  *B60W 40/08* (2012.01)
  *G06V 20/59* (2022.01)

(52) U.S. Cl.
  CPC ............ *B60W 30/00* (2013.01); *B60W 40/08* (2013.01); *B60W 2040/0872* (2013.01); *B60W 2420/403* (2013.01); *B60W 2520/00* (2013.01); *B60W 2540/22* (2013.01); *B60W 2540/221* (2020.02); *G06V 20/597* (2022.01)

(58) Field of Classification Search
  CPC ..... B60W 2040/0872; B60W 2520/00; B60W 2540/22; A61B 5/369; A61B 5/165; A61B 5/18; A61B 5/7221; G06V 20/597
  USPC .......................................................... 701/117
  See application file for complete search history.

(56) References Cited

U.S. PATENT DOCUMENTS

| | | | | |
|---|---|---|---|---|
| 10,807,527 | B1* | 10/2020 | Mauricia | B60Q 9/00 |
| 10,816,978 | B1* | 10/2020 | Schwalb | G08G 1/012 |
| 2008/0262335 | A1* | 10/2008 | Sun | A61N 1/0472 |
| | | | | 600/386 |
| 2009/0234552 | A1* | 9/2009 | Takeda | G08G 1/167 |
| | | | | 701/1 |
| 2011/0279676 | A1* | 11/2011 | Terada | A61B 5/369 |
| | | | | 348/148 |
| 2015/0310750 | A1* | 10/2015 | Glaunsinger | A61B 5/164 |
| | | | | 434/258 |
| 2017/0232967 | A1* | 8/2017 | Tomatsu | G08G 1/096783 |
| | | | | 701/117 |
| 2018/0188807 | A1* | 7/2018 | Cimenser | A61B 5/18 |
| 2019/0101985 | A1* | 4/2019 | Sajda | G06F 3/017 |
| 2019/0239795 | A1* | 8/2019 | Kotake | A61B 5/7267 |
| 2019/0303759 | A1* | 10/2019 | Farabet | G05D 1/00 |
| 2020/0172091 | A1* | 6/2020 | Takasaki | G08G 1/0145 |
| 2020/0241525 | A1* | 7/2020 | Harbour | G06F 3/014 |
| 2021/0048815 | A1* | 2/2021 | McErlean | B60W 50/14 |
| 2021/0089039 | A1* | 3/2021 | Schultz | B60W 60/0011 |
| 2021/0097311 | A1* | 4/2021 | McBeth | H04W 4/80 |
| 2021/0221404 | A1* | 7/2021 | Reiner | G05D 1/0055 |

FOREIGN PATENT DOCUMENTS

| | | |
|---|---|---|
| KR | 1020170046340 | 6/2017 |
| WO | WO2011045936 A1 | 4/2011 |

* cited by examiner

-9.3μN          -0.6μN

-1.8μN          13.0μN

FIG. 10A
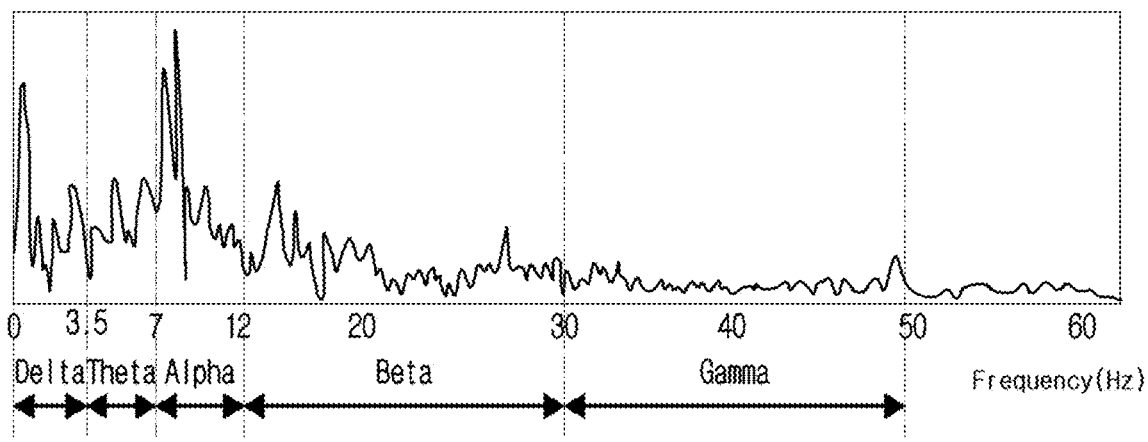
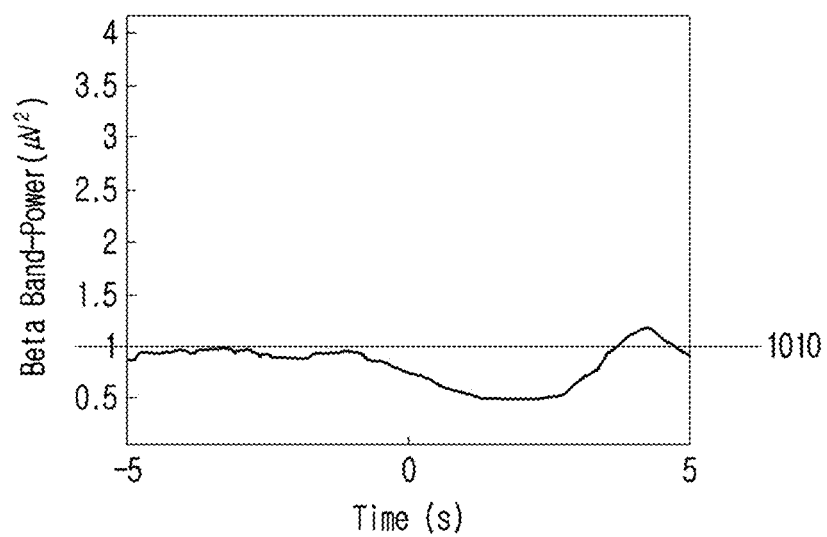
FIG. 10B

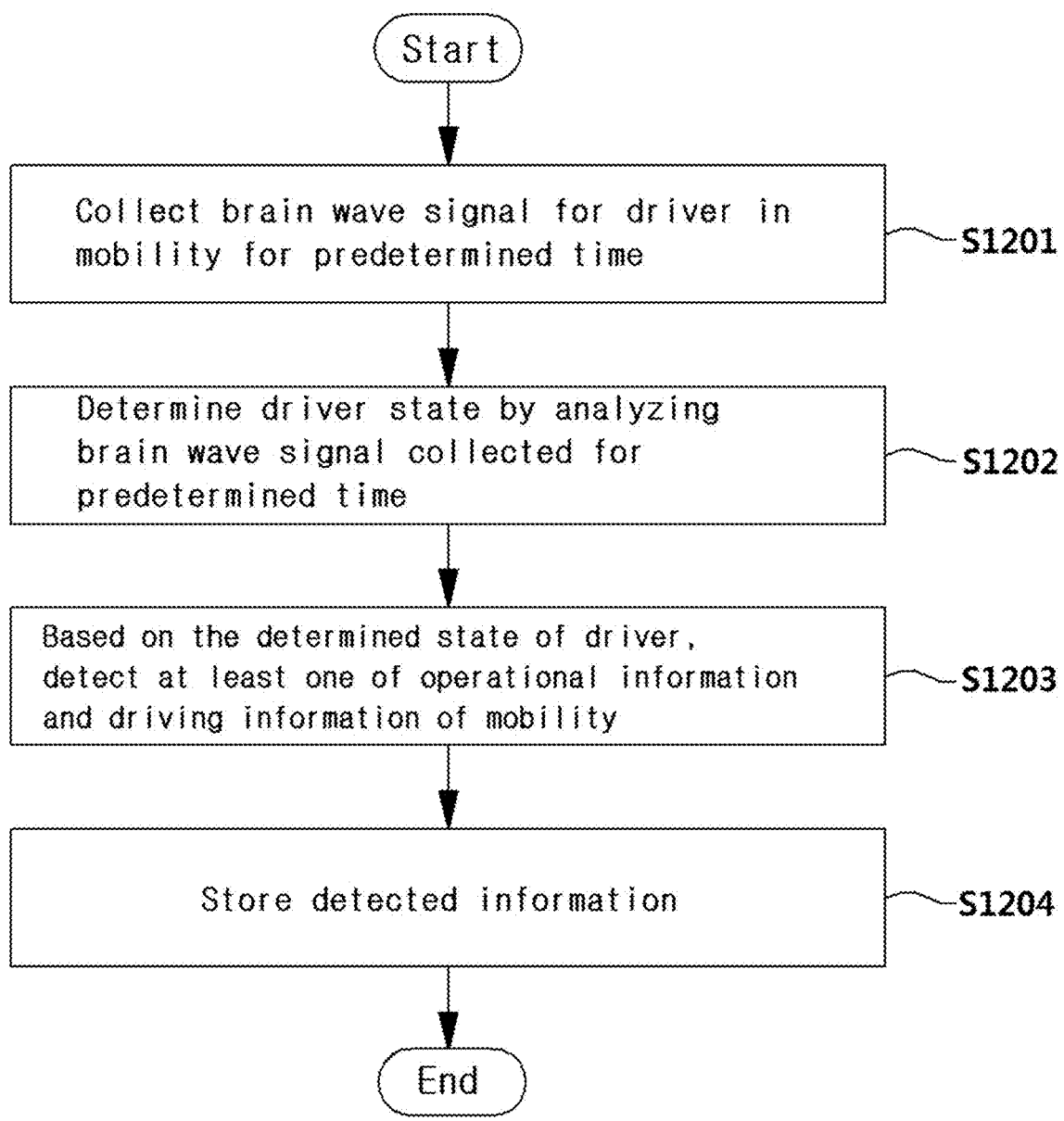

APPARATUS AND METHOD FOR GENERATING DRIVER SKILLED DRIVING MODEL USING ERROR MONITORING

CROSS REFERENCE TO RELATED APPLICATIONS

The present application claims priority to and the benefit of Korean Patent Application No. 10-2019-0131118, filed Oct. 22, 2019, which is incorporated herein for all purposes by this reference in its entirety.

TECHNICAL FIELD

The present disclosure relates to a mobility controlling method and apparatus. More particularly, the present disclosure relates to a mobility controlling method and apparatus based on error monitoring.

BACKGROUND

The statements in this section merely provide background information related to the present disclosure and may not constitute prior art.

As one of the transport means, a vehicle (or mobility) is a tool for living a life in the modern world. Furthermore, a vehicle itself may be regarded as something that gives meaning to someone.

As technology is advanced, functions provided by a vehicle also gradually evolve. For example, in recent years, vehicles not only transport a passenger to a destination, but also meet a passenger's needs for faster and safer travel to a destination. In addition, new devices are being added to vehicle systems in order to satisfy a passenger's aesthetic taste and comfort. In addition, the existing devices like steering wheels, transmissions, and acceleration/deceleration devices are also being developed so that more functions can be provided to users.

Meanwhile, a brain-computer interface or a brain-machine interface is a field of controlling a computer or a machine according to a person's intention by using brain wave signals. ERP (Event-Related Potential) is closely related to cognitive functions.

SUMMARY

An object of the present disclosure is to provide an apparatus and method for generating a driver skilled driving model.

Another object of the present disclosure is to provide an apparatus and method for modeling an operation or a driving situation of a mobility on the basis of a driver's state.

Yet another object of the present disclosure is to provide an apparatus and method for determining a driver's state by using error monitoring.

Yet another object of the present disclosure is to provide an apparatus and method for detecting an operation or a driving situation of a mobility on the basis of a driver's state.

The technical objects of the present disclosure are not limited to the above-mentioned technical objects, and other technical objects that are not mentioned will be clearly understood by those skilled in the art through the following descriptions.

The present disclosure may provide a driving model generation apparatus including a sensor that collects a brain wave signal for a driver in a mobility for a predetermined time, an analysis unit that determines the driver's state by analyzing the brain wave signal collected for the predetermined time and detects at least one of operational information and driving information of the mobility on the basis of the determined state of the driver, and a storage that stores the detected information. The brain wave signal includes an event-related potential (ERP), and the analyzer determines whether or not the driver is in an unstable state by analyzing the ERP.

According to one embodiment, the event-related potential (ERP) may include at least one of error-related negativity (ERN) and error positivity (Pe).

According to one embodiment, the event-related potential (ERP) may further include at least one of correct-related negativity (CRN) and correct positivity (Pc).

According to one embodiment, the analysis may compare an amplitude of the event-related potential, which is collected for the predetermined time, and a first threshold.

According to one embodiment, the first threshold may be differently determined according to at least one of a type of the ERP and a driver from whom the ERP is obtained.

According to one embodiment, the analyzer may classify the brain wave signal collected for the predetermined time according to each frequency band, and further determine whether or not the driver is an unstable state by comparing an amplitude of the classified brain wave signal at each frequency band and a second threshold.

According to one embodiment, the classified brain wave signal at each frequency band may include at least one of a theta wave, an alpha wave, and a beta wave.

According to one embodiment, the second threshold may be differently determined according to a type of the brain wave signal at each frequency band.

According to one embodiment, when an analysis result of the ERP and an analysis result of the brain wave signal at each frequency band show that the driver is in an unstable state, the analyzer may finally determine that the driver is in an unstable state.

According to one embodiment, the sensing unit may further include at least one of a speed measuring unit, an image acquisition unit, a sound acquisition unit, a wheel monitoring unit, and a manipulation apparatus unit, which are included in the mobility.

According to one embodiment, when the driver's state is determined as an unstable state, the analyzer may detect at least one of operational information and driving information of the mobility by using at least one of a speed measuring unit, an image acquisition unit, a sound acquisition unit, a wheel monitoring unit, and a manipulation apparatus unit, which are included in the mobility.

According to one embodiment, the storage may include at least one of the detected operational information and driving information of the mobility, the operational information of the mobility may include an operation of the mobility and at least one of a location, a date, time, a speed and an image corresponding to the operation, and the driving information of the mobility may include a driving path of the mobility and at least one event that is being performed by the mobility.

According to one embodiment, a simulation unit may be further included which models a driving path, and the simulation unit may model at least one of a driving situation and an operation of a mobility based on which the driver's state has been determined as an unstable state.

According to one embodiment, for a predetermined operation of a mobility based on which the driver's state has been determined as an unstable state, the simulation unit may model a virtual driving situation related to the predetermined operation.

In addition, the present disclosure may provide a driving model generation method that includes sensing to collect a brain wave signal for a driver in a mobility for a predetermined time, determining the driver's state by analyzing the brain wave signal collected for the predetermined time, detecting at least one of operational information and driving information of the mobility on the basis of the determined state of the driver, and storing the detected information. The brain wave signal includes an event-related potential (ERP), and the determining step includes determining whether or not the driver is in an unstable state by analyzing the ERP.

According to one embodiment, the event-related potential (ERP) may include at least one of error-related negativity (ERN) and error positivity (Pe).

According to one embodiment, the event-related potential (ERP) may further include at least one of correct-related negativity (CRN) and correct positivity (Pc).

According to one embodiment, the analysis may compare an amplitude of the event-related potential, which is collected for the predetermined time, and a first threshold.

According to one embodiment, the first threshold may be differently determined according to at least one of a type of the ERP and a driver from whom the ERP is obtained.

According to one embodiment, the determining step may further include classifying a brain wave signal collected for the predetermined time according to frequency band and determining whether or not the driver is in an unstable state by comparing an amplitude of the classified brain wave signal at each frequency band and a second threshold.

According to one embodiment, the classified brain wave signal at each frequency band may include at least one of a theta wave, an alpha wave, and a beta wave.

According to one embodiment, the second threshold may be differently determined according to a type of the brain wave signal at each frequency band.

According to one embodiment, the determining step may further include finally determining that the driver is in an unstable state, when an analysis result of the ERP and an analysis result of the brain wave signal at each frequency band show that the driver is in an unstable state.

According to one embodiment, the sensing step may further include at least one of a speed measuring unit, an image acquisition unit, a sound acquisition unit, a wheel monitoring unit, and a manipulation apparatus unit, which are included in the mobility.

According to one embodiment, the detecting step may include detecting at least one of operational information and driving information of the mobility by using at least one of a speed measuring unit, an image acquisition unit, a sound acquisition unit, a wheel monitoring unit, and a manipulation apparatus unit, which are included in the mobility.

According to one embodiment, the storing step may include storing at least one of the detected operational information and driving information of the mobility, the operational information of the mobility may include an operation of the mobility and at least one of a location, a date, time, a speed and an image corresponding to the operation, and the driving information of the mobility may include a driving path of the mobility and at least one event that is being performed by the mobility.

According to one embodiment, a simulation step may be further included which models a driving path, and the simulation step may include modeling at least one of a driving situation and an operation of a mobility based on which the driver's state has been determined as an unstable state.

According to one embodiment, for a predetermined operation of a mobility based on which the driver's state has been determined as an unstable state, the simulation step may include modeling a virtual driving situation related to the predetermined operation.

The features briefly summarized above with respect to the present disclosure are merely exemplary aspects of the detailed description below of the present disclosure, and do not limit the scope of the present disclosure.

BRIEF DESCRIPTION OF THE FIGURES

In order that the disclosure may be well understood, there will now be described various forms thereof, given by way of example, reference being made to the accompanying drawings, in which:

FIGS. 10A and 10B are views illustrating a process of comparing a brain wave signal at each frequency band and a predetermined threshold according to one embodiment of the present disclosure.

FIG. 12 is a flowchart illustrating a driving model generation method using error monitoring according to one embodiment of the present disclosure.

DETAILED DESCRIPTION

Figure 1:
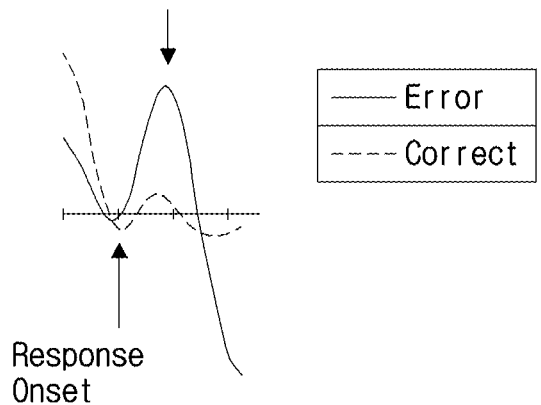
FIG. 1 is a view illustrating a general waveform of ERN in one form of the present disclosure.

The following description is merely exemplary in nature and is not intended to limit the present disclosure, application, or uses. It should be understood that throughout the drawings, corresponding reference numerals indicate like or corresponding parts and features.

Exemplary forms of the present disclosure will be described in detail such that the ordinarily skilled in the art would easily understand and implement an apparatus and a method provided by the present disclosure in conjunction with the accompanying drawings. However, the present disclosure may be embodied in various forms and the scope of the present disclosure should not be construed as being limited to the exemplary forms.

In describing forms of the present disclosure, well-known functions or constructions will not be described in detail when they may obscure the spirit of the present disclosure.

In the present disclosure, it will be understood that when an element is referred to as being "connected to", "coupled to", or "combined with" another element, it can be directly connected or coupled to or combined with the another element or intervening elements may be present therebetween. It will be further understood that the terms "comprises", "includes", "have", etc. when used in the present disclosure specify the presence of stated features, integers, steps, operations, elements, components, and/or combinations thereof but do not preclude the presence or addition of one or more other features, integers, steps, operations, elements, components, and/or combinations thereof.

It will be understood that, although the terms "first", "second", etc. may be used herein to describe various elements, these elements should not be limited by these terms. These terms are only used to distinguish one element from another element and not used to show order or priority among elements. For instance, a first element discussed below could be termed a second element without departing from the teachings of the present disclosure. Similarly, the second element could also be termed as the first element.

In the present disclosure, distinguished elements are termed to clearly describe features of various elements and do not mean that the elements are physically separated from each other. That is, a plurality of distinguished elements may be combined into a single hardware unit or a single software unit, and conversely one element may be implemented by a plurality of hardware units or software units. Accordingly, although not specifically stated, an integrated form of various elements or separated forms of one element may fall within the scope of the present disclosure. Also, the terms, such as 'unit' or 'module', etc., should be understood as a unit that processes at least one function or operation and that may be embodied in a hardware manner (e.g., a processor), a software manner, or a combination of the hardware manner and the software manner.

In the present disclosure, all of the constituent elements described in various forms should not be construed as being essential elements but some of the constituent elements may be optional elements. Accordingly, forms configured by respective subsets of constituent elements in a certain form also may fall within the scope of the present disclosure. In addition, forms configured by adding one or more elements to various elements also may fall within the scope of the present disclosure.

As an electrical activity of neurons constituting a brain, a brain wave signal (or brain signal, brain wave) means a bio signal that directly and indirectly reflects a conscious or unconscious state of a person. A brain wave signal can be measured in every area of human scalp, and its wavelength has a frequency of mainly 30 Hz or below and a potential difference of scores of microvolts. Depending on brain activity and state, various waveforms may appear. A research on interface control using a brain wave signal according to a person's intention is under way. A brain wave signal may be obtained by using EEG (Electro Encephalo Graphy) using electrical signals caused by brain activities, MEG (Magneto Encephalo Graphy) using magnetic signals occurring with electrical signals, and fMRI (functional Magnetic Resonance Imaging) or fNIRS (Near-Infrared Spectroscopy) using a change of oxygen saturation in the blood. Although fMRI and fNIRS are useful techniques for measuring brain activities, fMRI has a low time-resolution and fNIRS has a low spatial-resolution in general. Due to these limitations, EEG signals are mostly used because of their portability and time-resolution.

A brain wave signal changes spatially and over time according to brain activity. As a brain wave signal is usually difficult to analyze and its waveform is not easy to visually analyze, various processing methods are proposed.

For example, according to the number of oscillations (frequency), brain wave signals may be classified based on frequency bands (Power spectrum classification). The classification considers a measured brain wave signal as a linear sum of simple signals at each specific frequency, decomposes the signal into each frequency component and indicates a corresponding amplitude. A brain wave signal at each frequency may be obtained by using pre-processing normally for noise elimination, the Fourier transform into frequency domain, and a band-pass filter (BPF).

More particularly, according to frequency band, brain waves may be classified into delta, theta, alpha, beta and gamma waves. Delta waves are brain waves with a frequency of 3.5 Hz or below and an amplitude of 20~200 μV, mainly appearing in normal deep sleep or newborns. In addition, delta waves may increase as our awareness of the physical world decreases. Generally, theta waves are brain waves with a frequency of 3.5~7 Hz, mainly appearing in emotionally stable states or in sleep.

In addition, theta waves are generated mainly in the parietal cortex and in the occipital cortex and may appear during calm concentration for recollecting a memory or meditating. In addition, the amplitude of theta waves may increase while stress occurs. Generally, alpha waves are brain waves with a frequency of 7~12 Hz, mainly appearing in relaxed and comfortable states. In addition, alpha waves are normally generated in the occipital cortex during rest and may diminish in sleep. Generally, beta waves are brain waves with a frequency of 12~30 Hz, mainly appearing in a state of tension, which is bearable enough, or while a certain level of attention is paid. In addition, beta waves are mainly generated in the frontal cortex and are related to an awakened state or concentrated brain activities, pathological phenomena and medicinal effects. Beta waves may appear in a wide area throughout the brain. In addition, specifically, the beta waves may be divided into SMR waves with a frequency of 12~15 Hz, mid-beta waves with a frequency of 15~18 Hz and high beta waves with a frequency of 20 Hz and above. As beta waves appear to be stronger under stress like anxiety and tension, they are called stress waves. Gamma waves are brain waves that generally have a frequency of 30~50 Hz, mainly appearing in a strongly excited state or during high-level cognitive information processing. In addition, gamma waves may appear in an awaking state of consciousness and during REM sleep and may also be overlapped with beta waves.

Each of the brain wave signals according to frequency band is associated with a specific cognitive function. For example, delta waves are associated with sleep, theta waves are associated with working memory, and alpha waves are associated with attention or inhibition. Thus, the property of a brain wave signal at each frequency band selectively displays a specific cognitive function. In addition, the brain wave signal at each frequency band may show a little different aspect in each measuring part on the surface of head. The cerebral cortex may be divided into frontal cortex, parietal cortex, temporal cortex and occipital cortex. These parts may have a few different roles. For example, the occipital cortex corresponding to the back of head has the primary visual cortex and thus can primarily process visual information. The parietal cortex located near the top of head has the somatosensory cortex and thus can process motor/sensory information. In addition, the frontal cortex can process information related to memory and thinking, and the temporal cortex can process information related to auditory sense and olfactory sense.

Meanwhile, for another example, a brain wave signal may be analyzed by using ERP (Event-Related Potential). ERP is an electrical change in a brain in association with a stimulus from outside or a psychological process inside. ERP means a signal including an electrical activity of the brain, which is caused by a stimulus including specific information (for example, image, voice, sound, command of execution, etc.) after a certain time since the stimulus is presented.

To analyze an ERP, a process of separating a signal from a noise is desired. An averaging method may be mainly used. Particularly, by averaging brain waves measured based on stimulus onset time, it is possible to remove brain waves, which are not related to a stimulus, and to pick out only a related potential, that is, a brain activity commonly associated with stimulus processing.

As ERP has a high time resolution, it is closely related to a research on cognitive function. ERP is an electrical phenomenon that is evoked by an external stimulus or is related to an internal state. According to types of stimuli, ERPs may be classified into auditory sense-related potentials, sight-related potentials, somatic sense-related potentials and olfactory sense-related potentials. According to properties of stimuli, ERPs may be classified into exogenous ERPs and endogenous ERPs. Exogenous ERPs have a waveform determined by an external stimulus, are related to automatic processing, and mainly appear in the initial phase of being given the stimulus. For example, exogenous ERPs are brainstem potentials. On the other hand, endogenous ERPs are determined by an internal cognitive process or a psychological process or state, irrespective of stimuli, and are related to 'controlled processing'. For example, endogenous ERPs are P300, N400, P600, CNV (Contingent Negative Variation), etc.

Names given to ERP peaks normally include a polarity and a latent period, and the peak of each signal has an individual definition and meaning. For example, the positive potential is P, the negative potential is N, and P300 means a positive peak measured about 300 ms after the onset of a stimulus. In addition, 1, 2, 3 or a, b, c and the like are applied according to the order of appearance. For example, P3 means a third positive potential in waveform after the onset of a stimulus.

Hereinafter, various ERPs will be described.

For example, N100 is related to a response to an unpredictable stimulus.

MMN (Mismatch Negativity) may be generated not only by a focused stimulus but also by non-focused stimulus. MMN may be used as an indicator for whether or not a sense memory (echoic memory) operates before initial attention. P300, which will be described below, appears in a process of paying attention and making judgment, while MMN is analyzed as a process occurring in the brain before paying attention.

For another example, N200 (or N2) is mainly generated according to visual and auditory stimuli and is related to short-term memory or long-term memory, which are types of memories after attention, along with P300 described below.

For yet another example, P300 (or P3) mainly reflects attention to a stimulus, stimulus cognition, memory search and alleviation of uncertain feeling and is related to perceptual decision distinguishing stimuli from outside. As the generation of P300 is related to a cognitive function, P300 is generated irrespective of types of presented stimuli. For example, P300 may be generated in auditory stimuli, visual stimuli and somatic stimuli. P300 is widely applied to a research on brain-computer interface.

For yet another example, N400 is related to language processing and is caused when a sentence or an auditory stimulus with a semantic error is presented. In addition, N400 is related to a memory process and may reflect a process of retrieving or searching information from long-term memory.

For yet another example, as an indicator showing reconstruction or recollective process, P600 is related to a process of processing a stimulus more accurately based on information stored in long-term memory.

For yet another example, CNV refers to potentials appearing for 200~300 ms and even for a few seconds in the later phase. It is also called slow potentials (SPs) and is related to expectancy, preparation, mental priming, association, attention and motor activity.

For yet another example, ERN (Error-Related Negativity) or Ne (error negativity) is an event-related potential (ERP) generated by a mistake or an error. It may occur when a subject makes a mistake in a sensorimotor task or a similar task. More particularly, when a subject cognizes a mistake or an error, ERN is generated and its negative peak appears mainly in the frontal and central zones for about 50~150 ms. Especially, it may appear in a situation, where a mistake related to motor response is likely to occur, and may also be used to indicate a negative self-judgment.

Hereinafter, the major features of ERN will be described in more detail.

FIG. 1 is a view illustrating a general waveform of ERN according to one form of the present disclosure.

Referring to FIG. 1, negative potential values are depicted above the horizontal axis, and positive potential values are depicted below the horizontal axis. In addition, it can be confirmed that an ERP with a negative peak value is generated within a predetermined time range after a response onset for an arbitrary motion. Herein, the response may mean a case where a mistake or an error is made (Error Response). In addition, the predetermined time range may be about 50~150 ms. Alternatively, the predetermined time range may be about 0~100 ms. Meanwhile, in the case of a correct response, an ERP is generated which has a relatively smaller negative peak than ERN.

As an ERP of initial negativity, ERN is time-locked until a response error occurs. In addition, ERN is known to reflect the reinforcement activity of a dopaminergic system related to behavioral monitoring. ERN includes the fronto-striatal loop including the rostral cingulate zone. Meanwhile, dopamine is associated with the reward system of brain that usually forms a specific behavior and motivates a person thereby providing pleasure and reinforced feelings. When a behavior obtaining an appropriate reward is repeated, it is learned as a habit. In addition, more dopamine is released through emotional learning, and a new behavior is attempted due to the release of dopamine. Thus, reward-driven learning is called reinforcement learning.

In addition, ERN may be generated in 0~100 ms after the onset of an erroneous response that is caused during an interference task (for example, Go-noGo task, Stroop task, Flanker task, and Simon task) through the frontal cortex lead.

In addition, together with CRN described below, ERN is known to reflect a general behavior monitoring system that can distinguish a right behavior and a wrong behavior.

In addition, the fact that ERN reaches a maximum amplitude at the frontal cortex electrode is known to reflect that an intracerebral generator is located in the rostral cingulate zone or the dorsal anterior cingulate cortex (dACC) zone.

In addition, ERN may show a change of amplitude according to a negative emotional state.

In addition, ERN may be reported even in a situation where behavioral monitoring is performed based on external evaluation feedback processing unlike internal motor expression, and may be classified as FRN described below.

In addition, ERN may be generated not only when having cognized a mistake or an error but also before cognizing the mistake or the error.

In addition, ERN may be generated not only as a response to his/her own mistake or error but also as a response to a mistake or error of others.

In addition, ERN may be generated not only as a response to a mistake or an error but also as a response to anxiety or stress for a predetermined performance task or object.

In addition, as a larger peak value of ERN is obtained, it may be considered as reflecting a more serious mistake or error.

Meanwhile, for yet another example, being an event-related potential (ERP) that is generated after ERN, Pe (Error Positivity) is an ERP with a positive value, which is generated mainly at the frontal cortex electrode in about 150~300 ms after a mistake or an error. Pe is known as a reaction that realizes a mistake or an error and pays more attention. In other words, Pe is related to an indicator of a conscious error information processing process after error detection. ERN and Pe are known as ERPs related to error monitoring.

Hereinafter, the major features of Pe will be described in more detail.

Figure 2:
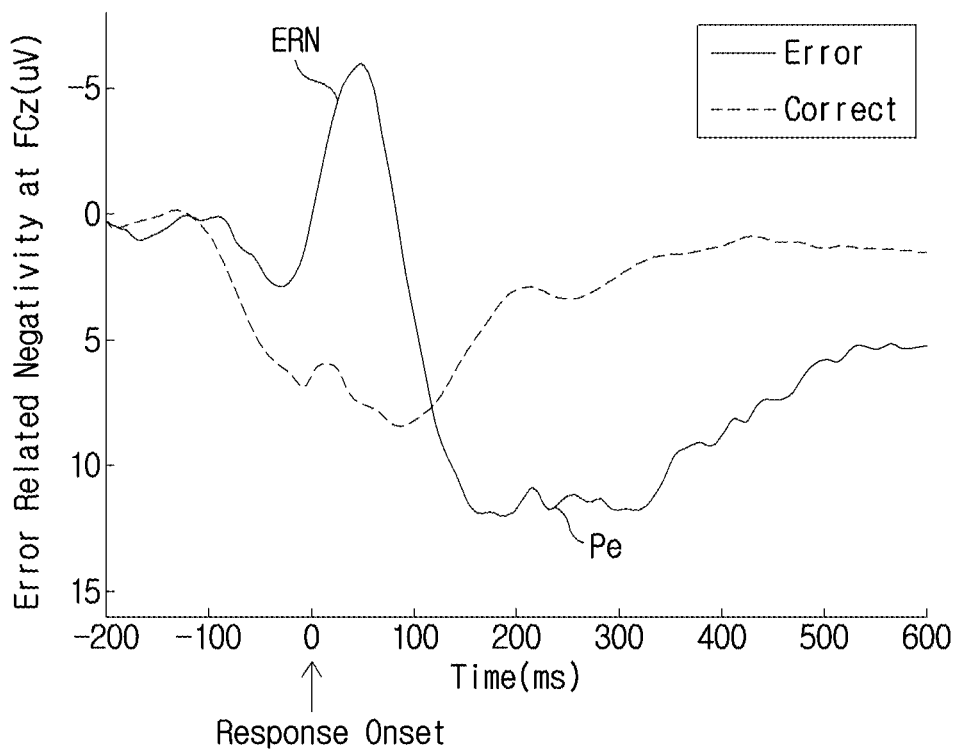
FIG. 2 is a view illustrating general waveforms of ERN and Pe according to one form of the present disclosure.

FIG. 2 is a view illustrating general waveforms of ERN and Pe according to another form of the present disclosure.

Referring to FIG. 2, negative potential values are depicted above positive potential values. In addition, it can be confirmed that an ERP with a negative peak value, that is, an ERN is generated within a first predetermined time range after a response onset for an arbitrary motion. Herein, the response may mean a case where a mistake or an error is made (Error Response). In addition, the first predetermined time range may be about 50~150 ms. Alternatively, the first predetermined time range may be about 0~200 ms.

In addition, it can be confirmed that an ERP with a positive peak value, that is, a Pe is generated within a second predetermined time range after the onset of the ERN. In addition, the second predetermined time range may be about 150~300 ms after an error onset. Alternatively, the second predetermined time range may mean about 200~400 ms.

Figure 3:
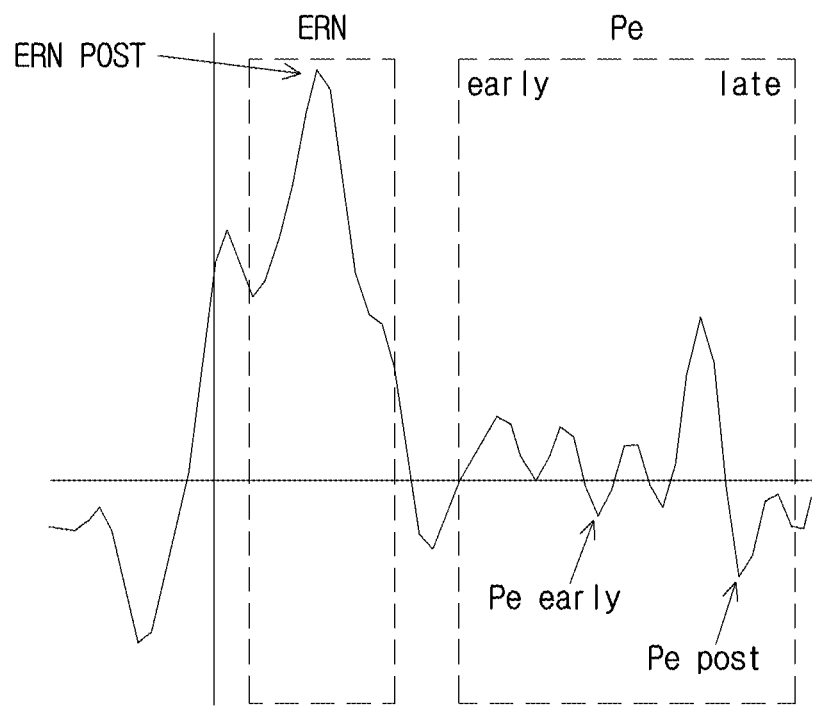
FIG. 3 is a view illustrating a deflection characteristic of Pe according to another form of the present disclosure.

FIG. 3 is a view illustrating a deflection characteristic of Pe in one form of the present disclosure.

Referring to FIG. 3, like P3, Pe has a wide deflection characteristic, and the plexus generator includes not only the areas of posterior cingulate cortex and insula cortex but also more anterior cingulate cortex.

In addition, Pe may reflect an emotional evaluation of an error and an attention to a stimulus like P300. In addition, ERN indicates a conflict between a right response and a wrong response, and Pe is known to be a response that realizes a mistake and pays more attention. In other words, ERN may be generated in a process of detecting a stimulus, and Pe may be generated depending on attention in a process of processing a stimulus. When ERN and/or Pe have relatively large values respectively, it is known that the values are related to an adaptive behavior intended to respond more slowly and more accurately after a mistake.

Figure 4A:
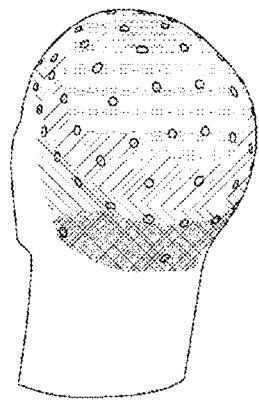
FIGS. 4A and 4B are views respectively illustrating measurement areas of ERP and Pe in one form of the present disclosure.
Figure 4B:
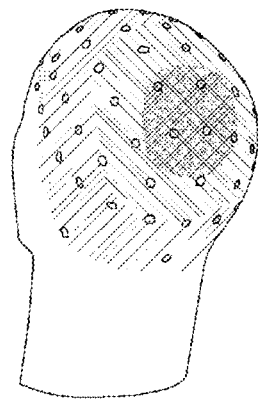

FIGS. 4A and 4B are views illustrating measurement areas of ERP and Pe according to one form of the present disclosure.

ERN and Pe are known as ERPs related to error monitoring. Regarding the measurement areas of ERN and Pe, a largest negative value and a largest positive value may normally be measured in the central area. However, there may be a little difference according to measurement conditions. For example, FIG. 4A is the main area where ERN is measured, and the largest negative value of ERN may normally be measured in the midline frontal or central zone (that is, FCZ). In addition, FIG. 4B is the main area where Pe is measured, and a large positive value of Pe may normally be measured in a posterior midline zone as compared to ERN.

Meanwhile, for yet another example, FRN (Feedback-Related Negativity) is an event-related potential (ERP) that is related to error detection obtained based on external evaluation feedback. ERN and/or Pe detect an error based on an internal monitoring process. However, in the case of FRN, when being obtained based on external evaluation feedback, it may operate similarly to the process of ERN.

In addition, FRN and ERN may share many electrophysiological properties. For example, FRN has a negative peak value at the frontal cortex electrode in about 250~300 ms after the onset of a negative feedback and may be generated in the dorsal anterior cingulate cortex (dACC) zone like ERN.

In addition, like ERN, FRN may reflect an activity of reinforcement learning by a dopaminergic system. In addition, FRN normally has a larger negative value than a positive feedback and may have a larger value for an unforeseen case than for a predictable result.

Figure 5:
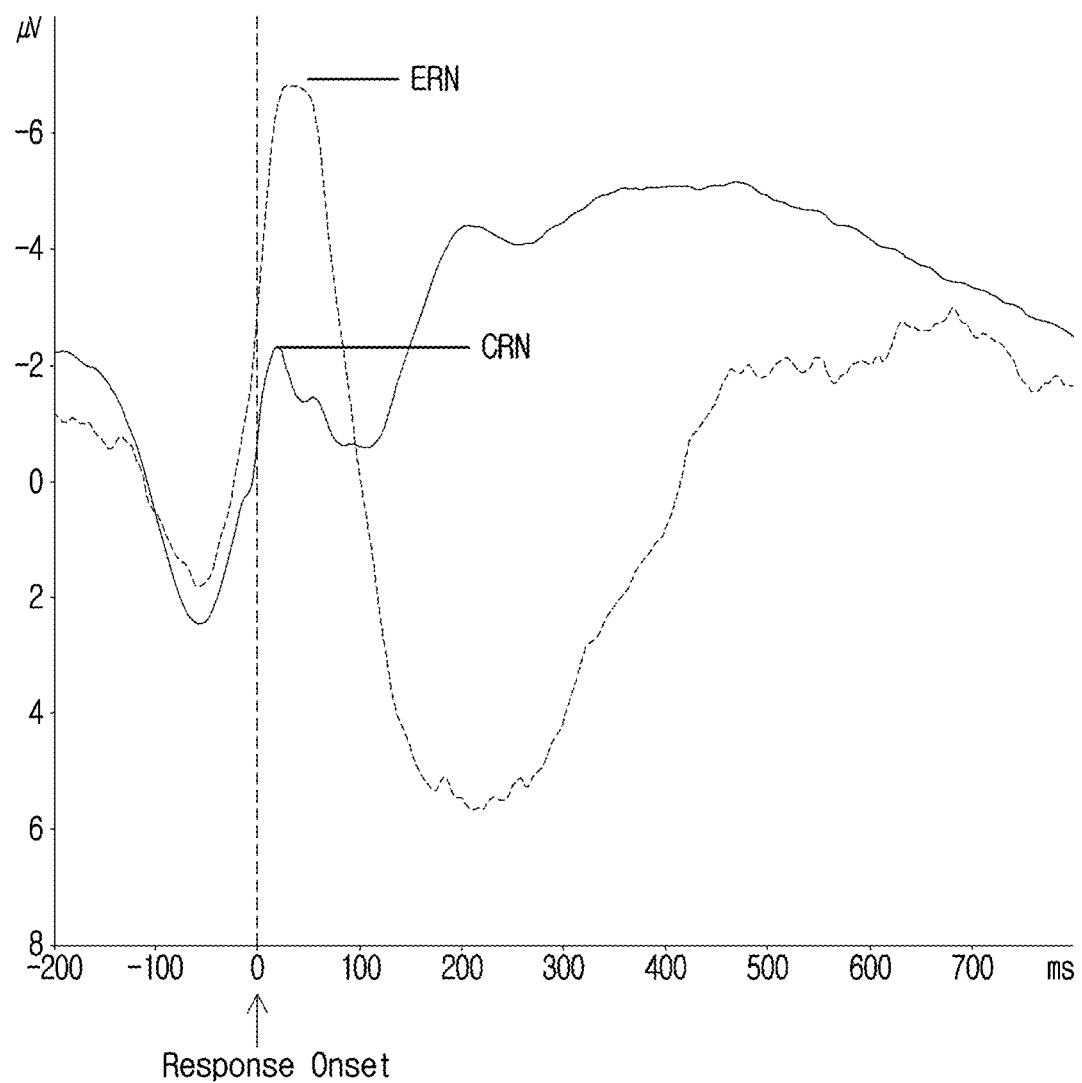
FIG. 5 is a view illustrating general waveforms of ERN and CRN according to one form of the present disclosure.

For yet another example, CRN (Correct-Related Negativity) is an ERP generated by a correct trial and is a negative value that is smaller than ERN. Like ERN, CRN may be generated in the initial latent period (for example, 0~100 ms). FIG. 5 is a view illustrating general waveforms of ERN and CRN in one form of the present disclosure.

For yet another example, Pc (Correct Positivity) is an event-related potential generated following CRN. It is an event-related potential generated in about 150~300 ms after the onset of correct response. The relation between CRN and Pc may be similar to the relation between ERN and Pe.

Meanwhile, ERPs may be classified into stimulus-locked ERPs and response-locked ERPs. The stimulus-locked ERPs and the response-locked ERPs may be divided according to criteria like evoking cause of ERP and response time. For example, an ERP evoked from a moment when a word or a picture is presented to a user from outside may be called a stimulus-locked ERP. In addition, for example, an ERP evoked from a moment when a user speaks or pushed a button may be called a response-locked ERP. Accordingly, based on the above-described criterion, in general, stimulus-locked ERPs are N100, N200, P2, P3, etc., and response-locked ERPs are ERN, Pe, CRN, Pc, FRN, etc.

Meanwhile, brain waves may be classified according to manifesting motives. Brain waves may be classified into spontaneous brain waves (spontaneous potentials) manifested by a user's will and evoked brain waves (evoked potentials) that are naturally manifested according to external stimuli irrespective of the user's will. Spontaneous brain waves may be manifested when a user moves on his/her own or imagines a movement, while evoked brain waves may be manifested by visual, auditory, olfactory and tactile stimuli, for example.

Meanwhile, brain wave signals may be measured in accordance with the International 10-20 system. The International 10-20 system determines measurement points of brain wave signals on the basis of the relationship between the location of an electrode and the cerebral cortex areas.

Figure 6:
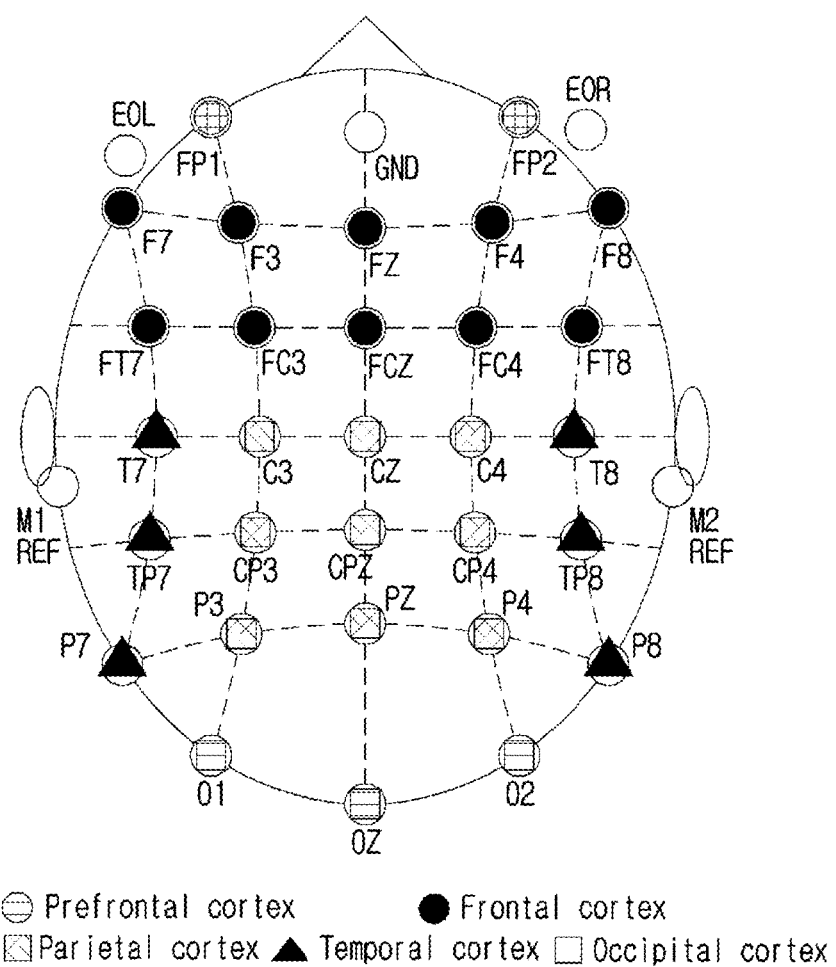
FIG. 6 is a view illustrating EEG measurement channels corresponding to cerebral cortex areas in one form of the present disclosure.

FIG. 6 is a view illustrating EEG measurement channels corresponding to the cerebral cortex areas according to one form of the present disclosure.

Referring to FIG. 6, brain areas (Prefrontal cortex FP1, FP2; Frontal cortex F3, F4, F7, F8, FZ, FC3, FC4, FT7, FT8, FCZ; Parietal cortex C3, C4, CZ, CP3, CP4, CPZ, P3, P4, PZ; Temporal cortex T7, T8, TP7, TP8, P7, P8; Occipital cortex O1, O2, OZ) correspond to 32 brain wave measurement channels. For each of the channels, data may be obtained and analysis may be performed for each cerebral cortex area by using the data.

Figure 7:
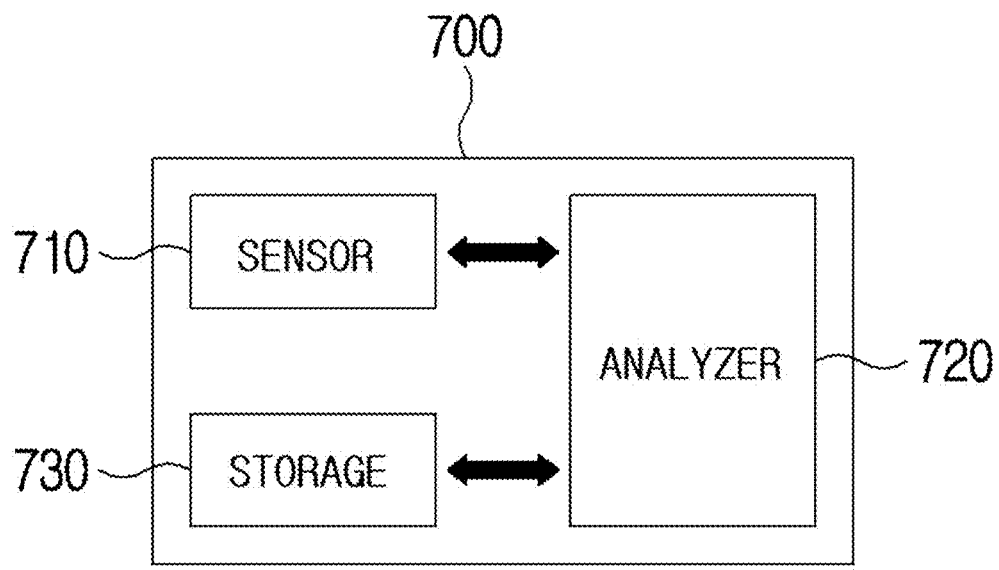
FIG. 7 is a block diagram illustrating a configuration of a driving model generation apparatus using error monitoring according to one embodiment of the present disclosure.

FIG. 7 is a block diagram illustrating a configuration of a driving model generation apparatus using error monitoring according to one embodiment of the present disclosure.

Traffic accidents are typically caused by human factors, vehicle factors and road environment factors. The majority of traffic accidents are caused by human factors. Particularly, human factors include a driver's mistake, carelessness, poor driving, sleepiness, drunkenness, and disobedience to traffic rules, and vehicle factors include defects in functions and negligence of maintenance. In addition, road environment factors include road designs, negligence of maintenance, construction, weather, visibility and lighting.

Meanwhile, human factors like a driver's mistake, carelessness and poor driving may be caused by insufficient driving practice, for example, when the driver has recently got his/her license.

For another example, when a driver takes a course for the first time, a human factor like poor driving may be generated.

For yet another, when a driver makes a particular movement to make a left turn or change lanes, a human factor like poor driving may be generated.

For yet another example, when driving on a familiar road close to home, a driver's carelessness may be generated.

Accordingly, when a driver can practice an operation or a driving situation, which the driver has no confidence in or feels anxious about, and thus human factors like poor driving, mistakes and carelessness can be removed, it may help reduce the probability of traffic accidents.

A response-locked ERP occurs when a mistake or an error is perceived. In addition, a response-locked ERP may be generated not only as a response to his/her own mistake or error but also as a response to a mistake or error of others. In addition, a response-locked ERP may be generated as a response to anxiety or stress for a predetermined performance task or object. Herein, a response-locked ERP may include ERN, Pe, CRN, Pc and FRN.

Meanwhile, while a driver drives a mobility, a drastic change in the driver's brain wave signal may be observed within a predetermined time range. In other words, as a brain wave signal is a bio signal that directly and indirectly reflects a conscious or unconscious state of a person, a driver's anxiety, stress or feeling for driving mistake or error while driving a mobility may cause a drastic change in the driver's brain wave signal. Although there may be diverse causes, the anxiety, stress or feeling for driving mistake or error may be generated mainly when a driver driving a mobility feels discomfort or difficulty in a movement, an operation, a driving environment and a road. Here, the movement, operation, driving environment and road may vary according to drivers.

For example, when changing lanes, a driver may feel anxious.

For another example, when making a permitted left turn, a driver may feel that a corresponding operation is difficult.

For yet another example, when driving on an overpass, a driver may get stressed out.

For yet another example, when driving on a sharp bend, a driver may feel that a corresponding operation is difficult.

For yet another example, when head in parking, a driver may feel that a corresponding operation is difficult.

In addition, brain wave signals classified according to frequency bands may reflect a driver's feelings like comfort, anxiety and stress.

For example, alpha waves are generally brain waves with a frequency of 8~12 Hz, mainly appearing in relaxed and comfortable states. In addition, alpha waves occur mainly in frontal lobe or occipital lobe and tend to diminish under stress.

For another example, beta waves are generally brain waves with a frequency of 13~30 Hz, mainly appearing in a state of tension, which is bearable enough, or while a certain level of attention is paid. In addition, beta waves mainly occur in frontal lobe and appear to be stronger under stress like anxiety and tension, thereby being referred to as stress waves.

For yet another example, theta waves are generally brain waves with a frequency of 3.5~7 Hz, mainly occurring in parietal lobe and occipital lobe. In addition, theta waves tend to increase under stress.

As described above, when no stress occurs, alpha waves may be measured as dominant signals. On the other hand, when stress occurs, alpha waves may diminish and beta waves and/or theta waves may be measured as dominant signals.

Consequently, when a brain wave signal collected from a driver for a predetermined time is analyzed, the driver's mental state may be determined. In other words, when a response-locked ERP generated as a response to anxiety, stress, mistake or error is obtained or amplitudes of brain wave signals like alpha waves, beta waves and theta waves are detected at each frequency, it may be determined whether a driver is in a stable or unstable state.

Meanwhile, the mobility may include a vehicle, a moving/transport apparatus and the like.

In addition, based on the driver's state thus determined, operational information and/or driving information of a mobility may be detected. Herein, the operational information and/or driving information of the mobility may be detected by using various sensing apparatuses included in the mobility.

Meanwhile, brain wave signals at each frequency may be classified into each section of frequency by extracting amplitudes of brain waves collected for a predetermined time in frequency domain and using a classification model like a support vector machine (SVM). The classification model is not limited to the above description and may include common methods for classifying brain wave signals.

Referring to FIG. 7, a driving model generation apparatus 700 may include a sensor 710, an analyzer 720 and/or a storage 730. It should be noted, however, that only some of the components necessary for explaining the present embodiment are illustrated and the components included in the driving model generation apparatus 700 are not limited to the above-described example. For example, two or more constituent units may be implemented in one constituent unit, and an operation performed in one constituent unit may be divided and executed in two or more constituent units. Also, some of the constituent units may be omitted or additional constituent units may be added.

A driving model generation method and/or apparatus of the present disclosure may determine a driver's state by analyzing a brain wave signal collected for a predetermined time for the driver of a mobility. In addition, the driving model generation method and/or apparatus may detect operational information and/or driving information of the mobility on the basis of the determined state of the driver. In addition, the driving model generation method and/or apparatus may generate a driving model reflecting a driving characteristic of the driver on the basis of the detected operational information and/or driving information of the mobility.

Particularly, the driving model generation apparatus 700 of the present disclosure may collect a brain wave signal for a driver of a mobility for a predetermined time. In addition, the sensor 710 may perform the operation.

Here, the brain wave signal may mean an ERP and/or a brain wave signal at each frequency.

Herein, the ERP may mean a response-locked ERP. In addition, the response-locked ERP may include ERN, Pe, CRN, Pc and FRN. In addition, apart from the ERN, Pe, CRN, Pc and FRN, other ERPs obtained after a response occurs (that is, response onset) may be included. In addition, the response-locked ERP may include a plural of ERPs.

In addition, herein, collecting the brain wave signal for a predetermined time may include a process of measuring a brain wave signal of a driver in a mobility and detecting an ERP from the measured brain wave signal.

In FIGS. 1 to 6, as described above, ERN, Pe, CRN, Pc and/or FRN may be generated as responses to wrong behaviors like an error or a mistake or responses to right behaviors. Accordingly, by using the ERP, it is possible to determine a driver's mental state like anxiety, stress and other feelings for mistake or error while driving a mobility. In addition, based on the determination, a driver-adaptive driving model may be generated.

For example, when a driver should change lanes, ERN and/or Pe may be generated.

For another example, when a driver should take an overpass, ERN and/or Pe may be generated.

For yet another example, when a driver is in traffic, takes a course for the first time or undergoes a tense and stressful situation on road, ERN and/or Pe may be generated.

For yet another example, when a driver should park a mobility head-in, ERN and/or Pe may be generated.

In addition, the predetermined time may mean about 0~400 ms after the onset of a specific response. In addition, the predetermined time may include a time range where the above-described response-locked ERP can be obtained. In addition, the predetermined time may vary according to the type of a response-locked ERP and may have a plural of time ranges. For example, a first time range may be given to obtain a first ERP, and a second time range may be given to obtain a second ERP.

Figure 8:
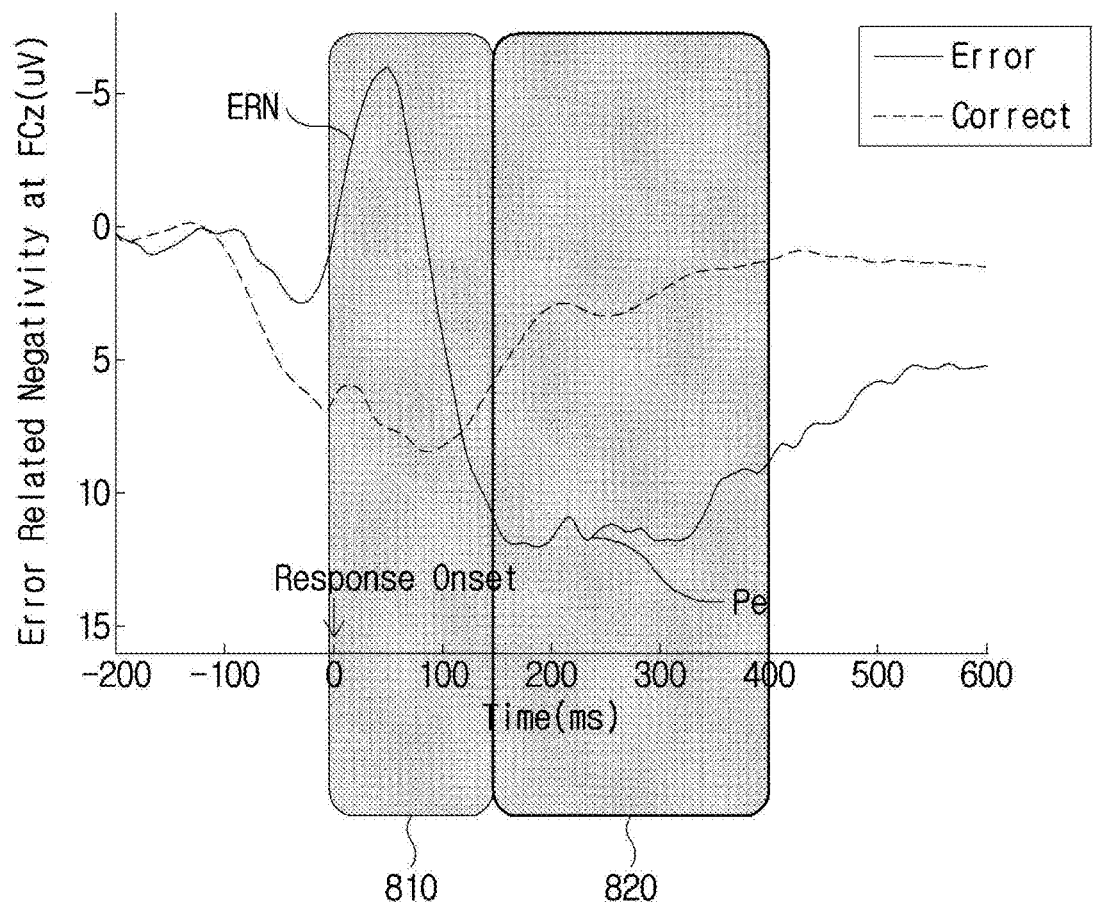
FIG. 8 is a view illustrating a measurement time range, when a target ERP is ERN and Pe, according to one embodiment of the present disclosure.

For example, when a first ERP is ERN and a second ERP is Pe, a first time range may be about 0~150 ms that is the main measurement section of ERN, and a second time range may be about 150~400 ms that is the main measurement section of Pe. FIG. 8 is a view illustrating a measurement time range, when a target ERP is ERN and Pe, according to one embodiment of the present disclosure. Referring to FIG. 8, ERN may be obtained in a first time range 810, and Pe may be obtained in a second time range 820.

For another example, when a first ERP is ERN and a second ERP is CRN, a first time range may be about 0~200 ms that is the main measurement section of ERN, and a second time range may be about 0~200 ms that is the main measurement section of CRN.

In addition, the brain wave signal for the driver may have been consecutively or periodically measured and stored.

The driving model generation apparatus 700 of the present disclosure may determine a driver's state by analyzing a brain wave signal that is collected for a predetermined time. In addition, the analyzer 720 may perform the operation.

Herein, the analysis may include a process of comparing an amplitude of ERP, which is collected for the predetermined time, and a predetermined threshold.

Figure 9:
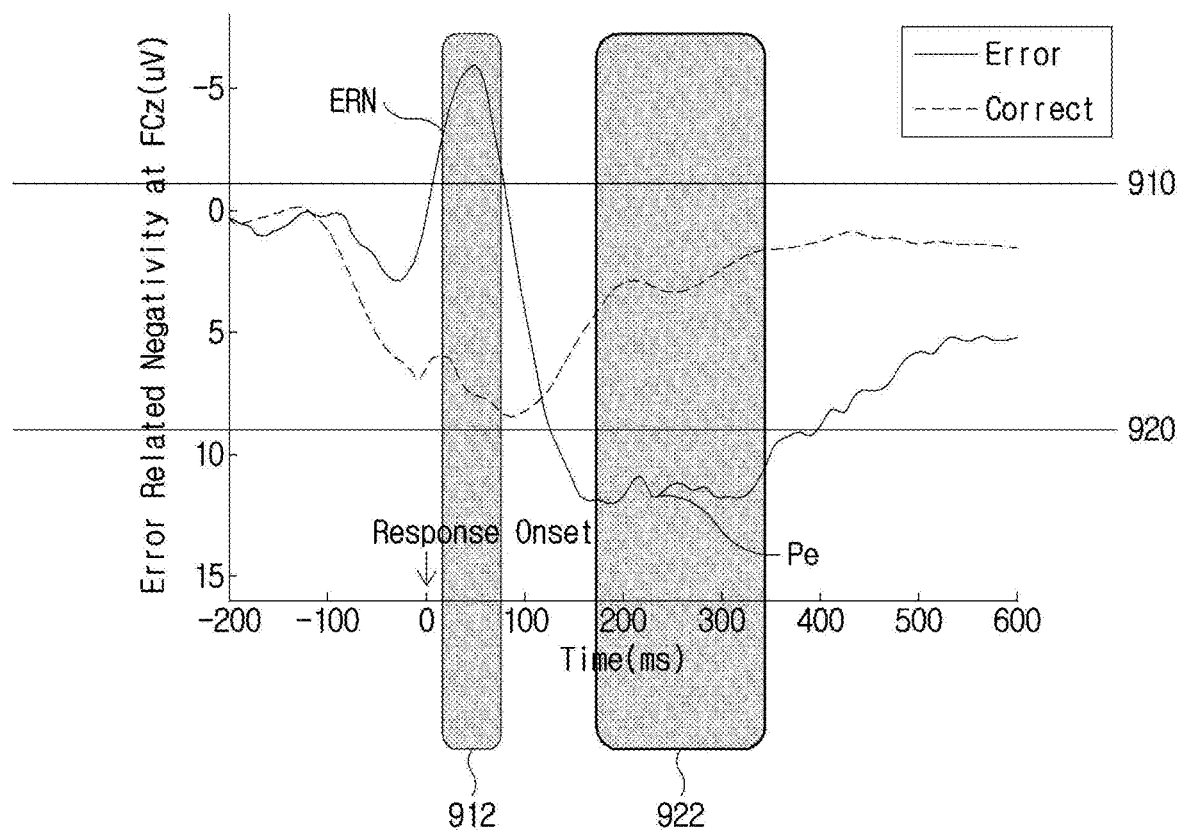
FIG. 9 is a view illustrating a process of comparing a target ERP and a predetermined threshold, when the target ERP is ERN and Pe respectively, according to one embodiment of the present disclosure.

Here, the threshold may be a preset value or a value input by a user. In addition, the threshold may have a different amplitude for each driver from whom an ERP is collected. For example, it may be a value reflecting the brain wave signal characteristic of each driver. In order to reflect an analysis result of the brain wave signal characteristic, a predetermined learning process may be performed in advance for response-locked ERP characteristics displayed in a driver's brain wave signal. In addition, the threshold may vary according to a type of ERP and may have a plural of values. FIG. 9 is a view illustrating a process of comparing a target ERP and a predetermined threshold, when the target ERP is ERN and Pe respectively, according to one embodiment of the present disclosure. Referring to FIG. 9, in the case of ERN, its amplitude may be compared with a first threshold 910. In the case of Pe, its amplitude may be compared with a second threshold 920. Herein, the amplitude may mean an absolute value.

In addition, the analysis may include a process of determining whether or not an amplitude of an ERP is equal to or greater than a predetermined threshold (that is, exceeds a predetermined threshold range) during a predetermined time interval. Referring to FIG. 9, in the case of ERN, the amplitude of ERN may be compared with a first threshold 910 to see whether or not the amplitude of ERN is equal to or greater than the first threshold 910 during a third time range 912. In the case of Pe, the amplitude of Pe may be compared with a second threshold 920 to see whether or not the amplitude of Pe is equal to or greater than the second threshold 920 during a fourth time range 922.

Meanwhile, the analysis may be preceded by a process of cognizing the onset of an ERP by using a time when a characteristic of a brain wave signal appears and/or using a pattern of the brain wave signal. In addition, the analysis may include a process of extracting an ERP.

In addition, meanwhile, an ERP used for the analysis may be a statistical value of ERP collected for a predetermined time. For example, the statistical value may mean an average value, a weighted average value, a maximum value, or a minimum value.

In addition, the analysis may determine a driver's state from a point where an amplitude of an ERP or an amplitude of a brain wave signal is equal to or greater than a predetermined threshold.

Here, the driver's state may include a stable state, an unstable state, etc.

As a peak value of ERP that is generally obtained is larger, a response-locked ERP may be considered as a response to a more serious mistake or error.

Accordingly, as described in FIG. 9, for example, in the case of ERN, when an amplitude of ERN is compared with the first threshold 910 during the third time range 912 and turns out to be equal to or greater than the first threshold 910, a driver's state may be determined as an unstable state.

For another example, when an amplitude of ERN is smaller than the first threshold 910, a driver's state may be determined as a stable state.

For yet another example, in the case of Pe, when an amplitude of Pe is equal or greater than the second threshold 920 during the fourth time range 922, a driver's state may be determined as an unstable state.

For another example, when an amplitude of Pe is smaller than the second threshold 920, a driver's state may be determined as a stable state.

For yet another example, when a peak value of ERP including ERN and/or Pe is equal to or greater than at least one of the first threshold 910 and the second threshold 920, a driver's state may be determined as an unstable state.

In addition, the analysis may be performed by using a brain wave signal template for each driver. Herein, a brain wave signal template may mean a brain wave signal in a time domain, which is obtained beforehand within a predetermined time range after a response onset for an arbitrary movement. The response may include an error, a mistake, a correct response and the like. The ready-made brain wave signal template may be scaled in the analysis process. In other words, the amplitude of a brain wave signal graph may be increased or decreased at a predetermined rate. For example, the analysis may be performed by comparing an amplitude-time graph waveform of a single ERP and/or a plural of ERPs obtained for a predetermined time with the brain wave signal template that is determined beforehand. The brain wave signal template may be obtained through a virtual simulation process or through a predetermined learning process.

In addition, the analysis may include a process of comparing an amplitude of brain wave signal at each frequency, which is collected for the predetermined time, and a predetermined threshold.

Here, the threshold may be a preset value or a value input by a user. In addition, the threshold may vary according to brain wave signal at each frequency. In addition, the threshold may be a predetermined value for a brain wave signal that appears either in a frequency domain or in a time domain.

FIGS. 10A and 10B are views illustrating a process of comparing a brain wave signal at each frequency band and a predetermined threshold according to one embodiment of the present disclosure.

For example, referring to FIG. 10A, when an amplitude of theta wave is equal to or greater than a predetermined threshold, a driver's state may be determined as an unstable state.

For another example, when an amplitude of alpha wave is smaller than a predetermined threshold, a driver's state may be determined as an unstable state.

For yet another example, when an amplitude of beta wave is equal to or greater than a predetermined threshold, a driver's state may be determined as an unstable state. Referring to FIG. 10B, in a time interval where an amplitude of beta wave is equal to or greater than a predetermined threshold 1010, a driver's state may be determined as an unstable state.

Meanwhile, a driver's state may be determined by combining brain wave signals at each frequency.

For example, when a ratio of beta wave to alpha wave in amplitude is equal to or greater than a predetermined threshold, a driver's state may be determined as an unstable state.

For another example, when a ratio of theta wave to alpha wave in amplitude is equal to or greater than a predetermined threshold, a driver's state may be determined as an unstable state.

For yet another example, when a ratio of a linear combination between theta wave and beta wave to alpha wave in amplitude is equal to or greater than a predetermined threshold, a driver's state may be determined as an unstable state.

Here, an amplitude of the brain wave signal at each frequency may mean a power of a frequency band within a predetermined range. In other words, the amplitude of the brain wave signal at each frequency may mean a power that is obtained by converting, for example, measured signals by Fourier transform into a frequency band in a frequency domain.

Meanwhile, whether a driver is in a stable state or unstable state may be ultimately determined by using an analysis result (hereinafter, 'first result') of an ERP that is collected for a predetermined time or an analysis result (hereinafter 'second result') of a brain wave signal at each frequency that is collected for a predetermined time or both.

For example, when both a first result and a second result are unstable states, a driver's state may be ultimately determined as an unstable state.

For another example, when at least one of a first result and a second result is an unstable state, a driver's state may be determined as an unstable state.

Meanwhile, a predetermined time for the first result and a predetermined time for the second result may be different from each other.

The driving model generation apparatus 700 of the present disclosure may detect operation and/or driving information of a mobility on the basis of a driver's state. In addition, the analyzer 720 may perform the operation.

The detecting may be performed from a point where an amplitude of an ERP or an amplitude of a brain wave signal is equal to or greater than a predetermined threshold.

For example, the driving model generation apparatus 700 may detect operational information and/or driving information of a mobility by using at least one sensing apparatus included in the mobility. Meanwhile, the sensor 710 may include the sensing apparatus.

Particularly, when a driver's state is determined as an unstable state, the driving model generation apparatus 700 may detect operational information and/or driving information of a mobility by using various sensing apparatuses included in the mobility.

Here, the sensing apparatuses may include a speed measuring apparatus, an image acquisition apparatus, a wheel monitoring apparatus, and a manipulation apparatus. The manipulation apparatus may monitor operations of a steering apparatus/an accelerator pedal/a brake pedal. The image acquisition apparatus may include a black box and a camera module.

Here, the operational information of the mobility may include operations of the mobility such as left turn, right turn, lane change, U-turn, acceleration and deceleration and time and locations where each of the operations occurs.

In addition, the driving information of the mobility may include a bend or an overpass where the mobility is running, a parking situation, or an event that is being performed by the mobility.

For example, when a driver's state is determined as an unstable state, the driving model generation apparatus 700 may detect that an operation of a mobility is a cornering operation like a right turn or a left turn, on the basis of a movement of a steering apparatus.

For another example, when a driver's state is determined as an unstable state, the driving model generation apparatus 700 may detect that a mobility is accelerating or decelerating, on the basis of a movement of an accelerator pedal and/or a brake pedal.

For yet another example, when a driver's state is determined as an unstable state, the driving model generation apparatus 700 may detect that a mobility is changing lanes, on the basis of a movement of a steering apparatus or a turn signal.

For yet another example, when a driver's state is determined as an unstable state, the driving model generation apparatus 700 may detect that a mobility is parking head-in, on the basis of an image obtained from an image acquisition apparatus.

The driving model generation apparatus 700 of the present disclosure may store the detected operational information and/or driving information of the mobility. In addition, the storage 730 may perform the operation.

The storing may be performed from a point where an amplitude of an ERP or an amplitude of a brain wave signal is equal to or greater than a predetermined threshold.

For example, the detected operational information and/or driving information of the mobility may be stored in a list form as shown in Table 1.

TABLE 1

| Operation | Driving information | Location | Date | Time | Speed (km/s) | Image |
|---|---|---|---|---|---|---|
| Left turn | | First location | First day | First time | First speed | First image |
| U-turn | | Second location | Second day | Second time | Second speed | Second image |
| Lane change | | Third location | Third day | Third time | Third speed | Third image |
| | Head-in parking | Fourth location | Fourth day | Fourth time | Fourth speed | Fourth image |
| | Overpass | Fifth location | Fifth day | Fifth time | Fifth speed | Fifth image |
| . . . | . . . | . . . | . . . | . . . | . . . | . . . |

In Table 1, an operation item may mean the detected operation of mobility. A driving information item may mean the detected driving path of a mobility or the detected event that is being performed by the mobility. Items of location, date, time, speed and image may mean a location, a date, a time, a speed, and an image respectively, where the detected operation of the mobility and/or the detected event of the mobility is being performed. Meanwhile, each item listed in Table 1 is only one embodiment but is not limited thereto, and necessary information for indicating an operation or an event performed by a mobility may be included in the item.

For another example, the detected operational information and/or driving information of the mobility may be arranged and stored in ascending/descending order based on the number of pieces of the operational or driving information.

Figure 11:
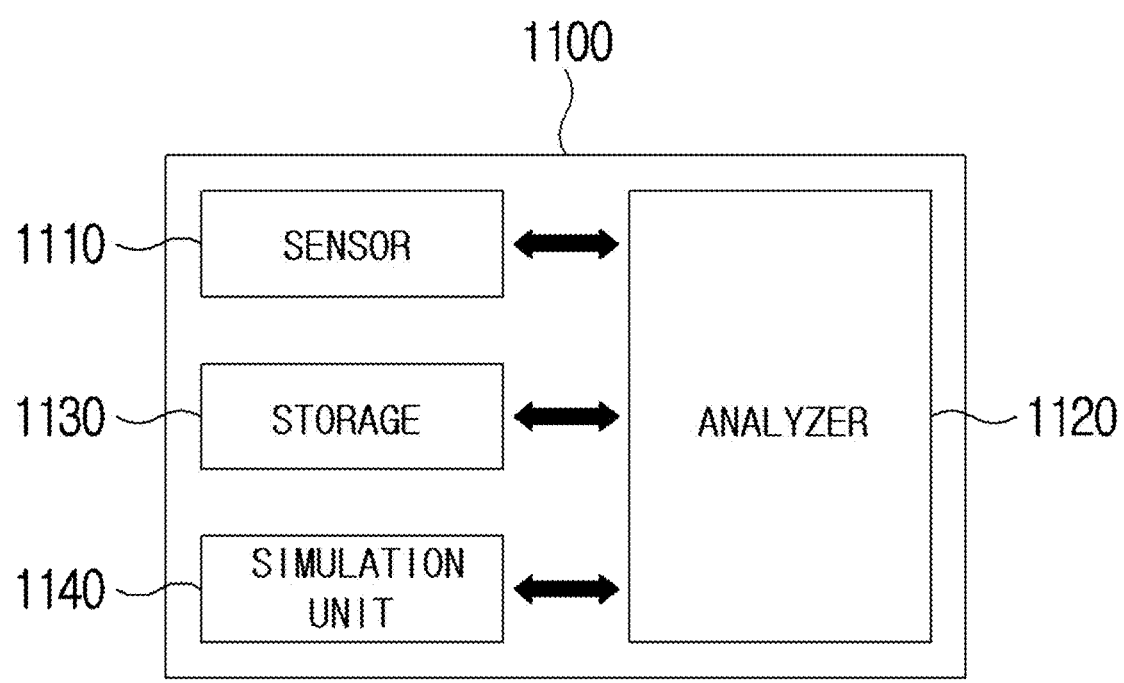
FIG. 11 is a block diagram illustrating a configuration of a driving model generation apparatus using error monitoring according to another embodiment of the present disclosure.

FIG. 11 is a block diagram illustrating a configuration of a driving model generation apparatus using error monitoring according to another embodiment of the present disclosure.

Referring to FIG. 11, a driving model generation apparatus 1100 may include a sensor 1110, an analyzer 1120, a storage 1130 and/or a simulation unit 1140. It should be noted, however, that only some of the components necessary for explaining the present embodiment are illustrated and the components included in the driving model generation apparatus 1100 are not limited to the above-described example. For example, two or more constituent units may be implemented in one constituent unit, and an operation performed in one constituent unit may be divided and executed in two or more constituent units. Also, some of the constituent units may be omitted or additional constituent units may be added.

The driving model generation apparatus 1100, the sensor 1110, the analyzer 1120 and the storage 1130 of FIG. 11 may be respective embodiments of the driving model generation apparatus 700, the sensor 710, the analyzer 720 and the storage 730 of FIG. 7.

The driving model generation apparatus 1100 of the present disclosure may generate a driving model by the operational information and/or driving information of a mobility, which is described in FIG. 7. In addition, the simulation unit 1140 may perform the operation.

For example, the driving model generation apparatus 1100 may model a whole path that has been passed by a driver.

For another example, the driving model generation apparatus 1100 may model an operational and/or driving situation of a mobility where a driver's state has been determined as an unstable state.

For yet another example, the driving model generation apparatus 1100 may model a whole path passed by a driver and provide a user with an operational and/or driving situation of a mobility where a driver's state has been determined as an unstable state within the modeled whole path. For example, a keyword like left turn, U-turn, lane change, head-in parking, and overpass, where a driver's state has been determined as an unstable state, may be provided to a user. Alternatively, a point where a driver's state has been determined as an unstable state may be indicated on the modeled whole path.

For another example, when an operation of a mobility where a driver's state has been determined as an unstable state was a situation of making a left turn, the driving model generation apparatus 1100 may model at least one virtual situation of making a left turn and provide a user with the modeled situation. The virtual situation of making a left turn may be obtained by using the detected information or through a virtual simulation process or a predetermined learning process.

For yet another example, when an operation of a mobility where a driver's state has been determined as an unstable state was a situation of head-in parking, the driving model generation apparatus 1100 may model at least one virtual situation of head-in parking and provide a user with the modeled situation. The virtual situation of head-in parking may be obtained by using the detected information or through a virtual simulation process or a predetermined learning process.

Accordingly, when a simulation program modeling an operational and/or driving situation, in which a driver's state has been determined as an unstable state, is provided to a user, the user may be able to repeatedly practice the simulation program, to improve driving habits, and further to prevent a traffic accident.

FIG. 12 is a flowchart illustrating a driving model generation method using error monitoring according to one embodiment of the present disclosure.

In the step S1210, a brain wave signal for a driver in a mobility may be collected for a predetermined time.

Here, the brain wave signal may include an ERP.

Meanwhile, the ERP may include at least one of error-related negativity (ERN) and error positivity (Pe). In addition, the ERP may further include at least one of correct-related negativity (CRN) and correct positivity (Pc).

In the step S1202, a driver's state may be determined by analyzing a brain wave signal that is collected for a predetermined time.

Herein, the analysis may include comparing an amplitude of ERP, which is collected for the predetermined time, and a first threshold.

Herein, the first threshold may be differently determined according to at least one of a type of the ERP and a driver from whom the ERP is obtained.

Herein, determining the driver's state may include analyzing the ERP to determine whether the driver is in an unstable state or in a stable state.

In addition, the determining of the driver's state may include classifying a brain wave signal collected for the predetermined time according to frequency band and determining whether the driver is in an unstable state or in a stable state by comparing an amplitude of the classified brain wave signal at each frequency band and a second threshold.

Meanwhile, the classified brain wave signal at each frequency band may include at least one of a theta wave, an alpha wave, and a beta wave.

Meanwhile, the second threshold may be differently determined according to a type of the brain wave signal at each frequency band.

In addition, the determining of the driver's state may include ultimately determining that the driver is in an unstable state, when an analysis result of the ERP and an analysis result of the brain wave signal at each frequency band show that the driver is in an unstable state.

In the step S1203, based on a determined state of the driver, at least one of operational information and driving information of a mobility may be detected.

Meanwhile, when the driver's state is determined as an unstable state, the detecting may include detecting at least one of operational information and driving information of the mobility by using at least one of a speed measuring unit, an image acquisition unit, a sound acquisition unit, a wheel monitoring unit, and a manipulation apparatus unit, which are included in the mobility.

In the step S1204, the detected information may be stored.

Meanwhile, the storing may include storing at least one of the detected operation information and the detected driving information of the mobility.

Herein, the operational information of the mobility may include an operation of the mobility and at least one of a location, a date, time, a speed, and an image that correspond to the operation.

Herein, the driving information of the mobility may include a driving path of the mobility and at least one event that is being performed by the mobility.

Meanwhile, the method may perform simulation for modeling a driving path, and the simulation may include modeling at least one of an operation and a driving situation of a mobility where the driver's state has been determined as an unstable state.

Meanwhile, for a predetermined operation of a mobility based on which the driver's state has been determined as an unstable state, the simulation may include modeling a virtual driving situation related to the predetermined operation.

According to the present disclosure, an apparatus and method for generating a driver skilled driving model may be provided.

In addition, according to the present disclosure, an apparatus and method for modeling an operation or a driving situation of a mobility on the basis of a driver's state may be provided.

In addition, according to the present disclosure, an apparatus and method for determining a driver's state by using error monitoring may be provided.

In addition, according to the present disclosure, an apparatus and method for detecting an operation or a driving situation of a mobility on the basis of a driver's state may be provided.

Effects obtained in the present disclosure are not limited to the above-mentioned effects, and other effects not mentioned above may be clearly understood by those skilled in the art from the following description.

Although exemplary methods of the present disclosure are described as a series of operation steps for clarity of a description, the present disclosure is not limited to the sequence or order of the operation steps described above. The operation steps may be simultaneously performed, or may be performed sequentially but in different order. In order to implement the method of the present disclosure, additional operation steps may be added and/or existing operation steps may be eliminated or substituted.

Various forms of the present disclosure are not presented to describe all of available combinations but are presented to describe only representative combinations. Steps or elements in various forms may be separately used or may be used in combination.

In addition, various forms of the present disclosure may be embodied in the form of hardware, firmware, software, or a combination thereof. When the present disclosure is embodied in a hardware component, it may be, for example, an application specific integrated circuit (ASIC), a digital signal processor (DSP), a digital signal processing device (DSPD), a programmable logic device (PLD), a field programmable gate array (FPGA), a general processor, a controller, a microcontroller, a microprocessor, etc.

The scope of the present disclosure includes software or machine-executable instructions (for example, operating systems (OS), applications, firmware, programs) that enable methods of various forms to be executed in an apparatus or on a computer, and a non-transitory computer-readable medium storing such software or machine-executable instructions so that the software or instructions can be executed in an apparatus or on a computer.

The description of the disclosure is merely exemplary in nature and, thus, variations that do not depart from the substance of the disclosure are intended to be within the scope of the disclosure. Such variations are not to be regarded as a departure from the spirit and scope of the disclosure.

The invention claimed is:

1. A driving model generation apparatus, the apparatus comprising:
   a sensor configured to collect a brain wave signal for a driver in a mobility for a predetermined time;
   an analyzer configured to determine a state of the driver by analyzing the brain wave signal collected for the predetermined time, and to detect at least one of operational information and driving information of the mobility based on the determined state of the driver;
   a storage configured to store the detected information; and
   a simulation unit configured to model a driving path;

wherein the brain wave signal comprises an event-related potential (ERP);

wherein the analyzer, by analyzing the ERP, determines whether or not the driver is in an unstable state; and wherein, for learning an operation of the mobility performed during the unstable state, the simulation unit models a virtual driving situation related to the operation of the mobility that has been performed by the driver during the unstable state.

2. The driving model generation apparatus of claim 1, wherein the ERP comprises at least one of error-related negativity (ERN), error positivity (Pe), correct-related negativity (CRN), and correct positivity (Pc).

3. The driving model generation apparatus of claim 1, wherein the analysis comprises comparing an amplitude of the ERP collected for the predetermined time and a first threshold.

4. The driving model generation apparatus of claim 3, wherein the first threshold is determined according to at least one of a type of the ERP and the driver's information.

5. The driving model generation apparatus of claim 1, wherein the analyzer classifies a brain wave signal collected for the predetermined time into a brain wave signal at each frequency band, and further determines whether or not the driver is an unstable state by comparing an amplitude of the classified brain wave signal at each frequency band and a second threshold.

6. The driving model generation apparatus of claim 1, wherein the sensor further comprises at least one of a speed measuring unit, an image acquisition unit, a sound acquisition unit, a wheel monitoring unit, and a manipulation apparatus unit that are comprised in the mobility.

7. The driving model generation apparatus of claim 6, wherein, when the driver's state is determined as an unstable state, the analyzer detects at least one of operational information and driving information of the mobility by using at least one of the speed measuring unit, the image acquisition unit, the sound acquisition unit, the wheel monitoring unit, and the manipulation apparatus unit that are comprised in the mobility.

8. The driving model generation apparatus of claim 1, wherein the storage comprises at least one of the detected operational information and driving information of the mobility;

wherein the operational information of the mobility comprises an operation of the mobility and at least one of a location, a date, time, a speed and an image corresponding to the operation; and wherein the driving information of the mobility comprises a driving path of the mobility and at least one event that is being performed by the mobility.

9. A driving model generation method, the method comprising:

collecting, via a sensor, a brain wave signal for a driver in a mobility for a predetermined time;

determining a state of the driver by analyzing the brain wave signal collected for the predetermined time;

detecting at least one of operational information and driving information of the mobility based on the determined state of the driver;

storing the detected information; and simulating to model a driving path;

wherein the brain wave signal comprises an event-related potential (ERP);

wherein the determining comprises determining, by analyzing the ERP, whether or not the driver is in an unstable state; and wherein, for learning an operation of the mobility performed during the unstable state, the simulation unit models a virtual driving situation related to the operation of the mobility that has been performed by the driver during the unstable state.

10. The driving model generation method of claim 9, wherein the ERP comprises at least one of error-related negativity (ERN), error positivity (Pe), correct-related negativity (CRN), and correct positivity (Pc).

11. The driving model generation method of claim 9, wherein the analysis comprises comparing an amplitude of the ERP collected for the predetermined time and a first threshold.

12. The driving model generation method of claim 11, wherein the first threshold is determined according to at least one of a type of the ERP and the driver's information.

13. The driving model generation method of claim 9, wherein the determining further comprises:

classifying the brain wave signal collected for the predetermined time into a brain wave signal at each frequency band; and determining whether or not the driver is in an unstable state by comparing an amplitude of the classified brain wave signal at each frequency band and a second threshold.

14. The driving model generation method of claim 9, wherein the sensor further comprises at least one of a speed measuring unit, an image acquisition unit, a sound acquisition unit, a wheel monitoring unit, and a manipulation apparatus unit that are comprised in the mobility.

15. The driving model generation method of claim 14, wherein, when the driver's state is determined as an unstable state, the detecting comprises detecting at least one of operational information and driving information of the mobility by using at least one of the speed measuring unit, the image acquisition unit, the sound acquisition unit, the wheel monitoring unit, and the manipulation apparatus unit that are comprised in the mobility.

16. The driving model generation method of claim 9, wherein the storing comprises storing at least one of the detected operational information and driving information of the mobility;

wherein the operational information of the mobility comprises an operation of the mobility and at least one of a location, a date, time, a speed and an image corresponding to the operation; and wherein the driving information of the mobility comprises a driving path of the mobility and at least one event that is being performed by the mobility.

* * * * *